(12) United States Patent
Bouvier et al.

(10) Patent No.: US 6,469,067 B1
(45) Date of Patent: Oct. 22, 2002

(54) COMBINATIONS

(75) Inventors: Jacques Bouvier, Neuchâtel; Catherine Kolly, St-Aubin, both of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/718,115

(22) Filed: Nov. 20, 2000

(30) Foreign Application Priority Data

Nov. 25, 1999 (EP) .............................. 99811085

(51) Int. Cl.[7] ........................ A61K 31/17; A61K 31/70
(52) U.S. Cl. ........................................ 514/596; 514/30
(58) Field of Search .................. 514/596, 30

(56) References Cited

U.S. PATENT DOCUMENTS 4,857,510 A   8/1989   Knauf et al. ................... 514/30

FOREIGN PATENT DOCUMENTS

| EP | 0 242 502 | 10/1987 |
| WO | WO 96/25852 | 8/1996 |

OTHER PUBLICATIONS

Resistance and the Control of Sheep Ectoparasites, Garry W. Levot—Nov. 1995—XP–000913722.

*Primary Examiner*—Kevin E. Weddington
(74) *Attorney, Agent, or Firm*—Michael U. Lee; John W. Kung

(57) ABSTRACT

An active ingredient combination for the simultaneous control of ecto- and endoparasites, especially mites, ticks and nematodes, on productive livestock, domestic animals and pets, is described, which comprises the active ingredients (1) 1-[4-chloro-3-(3-chloro-5-trifluoromethyl-2-pyridyloxy)phenyl]-3-(2,6-difluorobenzoyl)urea and (2) a compound of formula (i)

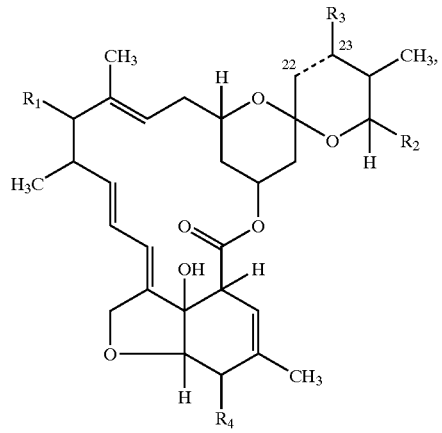

wherein
$R_1$ is hydrogen or one of radicals

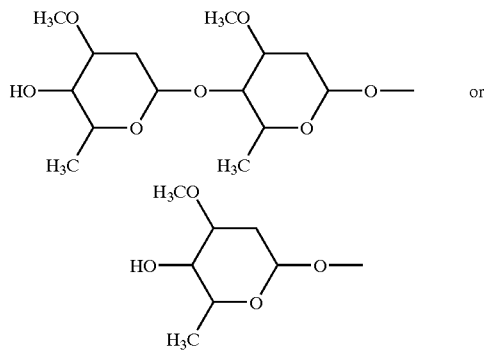

$R_2$ is —CH(CH$_3$)—CH$_3$, —CH(CH$_3$)—C$_2$H$_5$, —C(CH$_3$)=CH—CH(CH$_3$)$_2$ or cyclohexyl; $R_3$ is hydrogen or hydroxy if the bond between atoms 22 and 23 represents a double bond, or is hydrogen or the group =N—O—CH$_3$ if a single bond is present between atoms 22 and 23; and $R_4$ is HO— or HO—N=, in free form or in the form of a physiologically acceptable salt.

13 Claims, No Drawings

COMBINATIONS

The present invention relates to preparations for veterinary medicine, which contain a combination of 1-[4-chloro-3-(3-chloro-5-trifluoromethyl-2-pyridyloxy)phenyl]-3-(2,6-difluorobenzoyl)urea [hereinafter compound (B)] and a further active ingredient of formula (i) below from the avermectin class. It also relates to the use of these two components in the production of veterinary preparations and their joint usage in a method of controlling ecto- and endo-parasites on productive livestock, domestic animals and pets.

1-[4-chloro-3-(3-chloro-5-trifluoromethyl-2-pyridyloxy)phenyl]-3-(2,6-difluorobenzoyl) including the preparation thereof, is known from European Published Specification EP-0.079,311. This compound has in the following the name "compound B".

In the context of the invention, the active ingredient from the avermectin class is a macro-cyclic compound of formula (i)

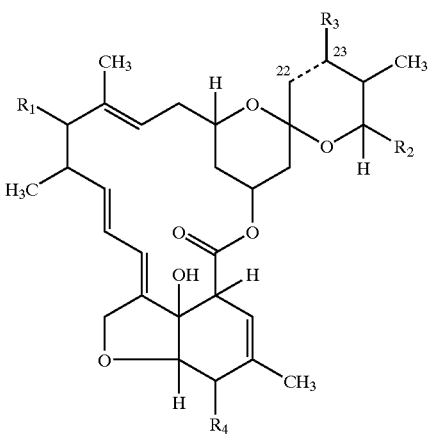

wherein $R_1$ is hydrogen or one of radicals

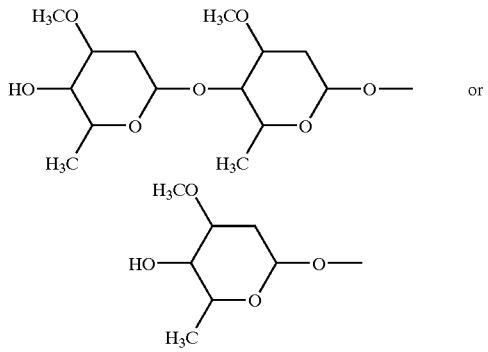

or $R_2$ is —CH(CH$_3$)—CH$_3$, —CH(CH$_3$)—C$_2$H$_5$, —C(CH$_3$)=CH—CH(CH$_3$)$_2$ or cyclohexyl; $R_3$ is hydrogen or hydroxy if the bond between atoms 22 and 23 represents a double bond, or is hydrogen or the group =N—O—CH$_3$ if a single bond is present between atoms 22 and 23; and $R_4$ is HO— or HO—N=, in free form or in the form of a physiologically acceptable salt.

Typical representatives of compounds of formula (i) are:
1) Ivermectin is a mixture of two compounds of formula (i), wherein $R_1$ is the radical

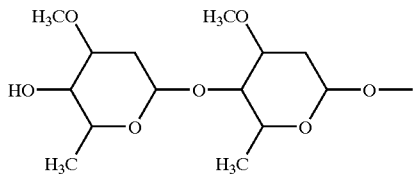

and $R_3$ is hydrogen steht, whereby atoms 22 and 23 are linked by a single bond and $R_2$ is either —CH(CH$_3$)—CH$_3$ or —CH(CH$_3$)—C$_2$H$_5$; both of them, including their preparation, are known from EP-0,001,689. Ivermectin is preferred in the context of the present invention.

2) Doramectin is a compound of formula (i), wherein $R_1$ is the radical

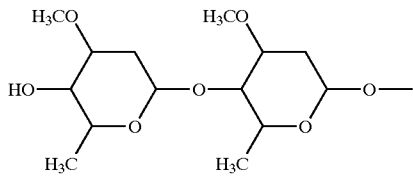

and $R_3$ is hydrogen, whereby atoms 22 and 23 are linked by a double bond and $R_2$ is cyclohexyl. Doramectin is described e.g. in EP-0,214,731 and EP-0,276,131.

3) Moxidectin, also known as LL-F28249α is a compound of formula (i), wherein $R_1$ and $R_3$ are hydrogen, whereby atoms 22 and 23 are linked by a single bond and $R_2$ signifies —C(CH$_3$)=CH—CH(CH$_3$)$_2$. Moxidectin is known from U.S. Pat. No. 4,916,154.

4) Selamectin is 25-cyclohexyl-25-de(1-methylpropyl)-5-deoxy-22,23-dihydro-5-(hydroxyimino)avermectin B1 monosaccharide and thus a compound of formula (i), wherein $R_1$ is the radical

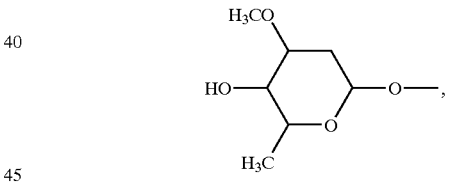

$R_2$ signifies cyclohexyl, $R_3$ is hydrogen, whereby atoms 22 and 23 are linked by a single bond and $R_4$ is HO—N=. Selamectin is known e.g. from: ECTOPARASITE ACTIVITY OF SELAMECTIN; A novel endectocide for dogs and cats. A Pfizer Symposium, held in conjunction with The 17th international Conference of the World Association for the Advancement of Veterinary Parasitology, Aug. 19, 1999. Copenhagen, Denmark.

The compounds of formula (i) are known from the said publications or are obtainable analogously to known agents.

As is known, the life cycles of the different parasites, which can infest humans or animals, are very complex, which makes it difficult to control them in many cases. In addition, multiple diseases are often a problem that has not yet been satisfactorily resolved. In particular in warmer regions, herd animals such as cattle and sheep, are often infected by an epidemic of helminths and other worm diseases. These diseases in themselves are frequently life-threatening. In many ways, these animals which are already weakened by the endoparasites are additionally infested by ectoparasites, in particular ticks, which often appear en mass and further weaken these animals and form an additional stress factor. The animals which are already weakened by the worms take up even less nourishment because of these plagues, lose weight even more rapidly and require intensive treatment and attention. Moreover, ticks may be infected with various kinds of pathogens, and transmit them particularly easily to host animals that are already weakened and whose immune system is also weakened. There is therefore a vital need to provide preparations which successfully eliminate both the parasitic worms and ticks.

Typical helminthic diseases in the context of the present invention are those caused by members of the nematode class. These include for example the families Filariidae and Setariidae, and the genera Haemonchus, Trichostrongylus, Ostertagia, Nematodirus, Cooperia, Ascaris, Bunostumum, Oesophagostonum, Chabertia, Trichuris, especially *Trichuris vulpis*, Strongylus, Trichonema, Dictyocaulus, Capillaria, Strongyloides, Heterakis, Toxocara, especially *Toxocara canis*, Acaridia, Oxyuris, Ancylostoma, especially *Ancylostoma caninum*, Uncinaria, Toxascaris and Paras- caris; Dirofilaria, especially *Dirofilaria immitis* (heartworm).

Ticks can feed exclusively from the blood of one host or also from the blood of different hosts. The attach themselves firmly to the host animal and suck its blood. The fully engorged females drop from the host animal and then lay a large number of eggs in a suitable niche in their surroundings. The developing larvae then search for a new host animal in order to develop into adults via the nymph stage, and in turn fully engorge themselves with blood. Certain species feed on two and some on three host animals during their lifecycle.

Ticks of importance in this instance are above all those which belong to the genera Amblyomma, Boophilus, Hyalomma, Ixodes, Rhipicephalus and Dermacentor, especially the species Boophilus microplus and *B. annulatus*, and most especially *B. microplus*. They are responsible for the transmission of numerous diseases which can affect humans and animals. The diseases which are mostly transmitted are bacterial, protozoan, rickettsial and viral. The pathogens of such diseases are transmitted especially by ticks which feed on more than one host. These diseases can lead to the debilitation or even death of the host animals. In most cases they cause considerable economic damage, for example by diminishing the value of meat from livestock, damaging the usable skin, or reducing milk production.

Ticks of the above species are traditionally controlled on otherwise healthy host animals by treating the infested animals with an acaricidally active composition depending on the type of infestation involved, i.e. by curative means. The occurrence of ticks, for example on pasture land, is heavily dependent, however, on seasonal weather conditions, and the ultimate infestation of the host animals itself depends also on their resistance to the ticks. This means that preventative control of the ticks is difficult and time-consuming, since inter alia the severity of infestation by the pests can only be estimated with difficulty. In the case of animals that have already been weakened by other parasites, e.g. the above-mentioned worms, effective control of the ticks is particularly important. Here, preparations are preferred, which show marked contact action, i.e. either kill the ticks upon contact with the pelt or skin, or induce them not to attach themselves and suck blood. With weakened animals, it is especially important that they are not additionally stressed by the anti-tick treatment, and that they are not treated with a number of veterinary preparations, the side effects of which might accumulate. Mass-produced, suitably-adapted, well-tolerated broad-band preparations might provide a remedy.

It is becoming increasingly difficult to synthesise or to isolate from natural sources new classes of active ingredient, which are equal to the active substances already available or even superior to them. Many of the known active ingredients in the field of animal health show exceptionally marked activity against certain target parasites. Unfortunately, their activity is usually restricted either to external or internal parasites only, or they have substantial gaps in their spectrum of activity in one respect or another. For treatment of already weakened animals, however, it would be desirable to provide broad-band preparations, which cover a broad spectrum of activity, are very well tolerated and can reduce the number of treatments to a minimum.

Instead of searching for new active ingredients, possibly for years without success, It may be preferable to attempt to achieve the desired broad-band effect by combining known active substances. At first appearance, this seems to be a simple task, since the spectra of activity of different classes of substances have been known for a long time. In reality however, the mere combination of two active substances seldom leads to the desired success, since the simultaneous administration of different active substances can lead to unpredictable kinetic and metabolic effects, not to mention potentiation of the undesired side effects. Also, contrary potentiating or diminishing effects are observed, and even undesired chemical reactions between the degradation products arising through the endogenous enzymes. Not all of the proposed combinations exhibit the desired broad-band spectrum upon practical application. In many cases, new deficiencies in efficacy occur, which render the preparation useless for the planned application or restrict it to specific cases, since one or other of the frequently appearing parasites is not covered or is unsufficiently covered, or the immune system of the treated animals is adversely affected, and they become susceptible to e.g. fungal diseases or other secondary infections, which makes their treatment more difficult and involves the usage of further veterinary preparations. A further difficulty is that helminthic infestations may be controlled particularly effectively if the corresponding preparations are administered systemically, i.e. either percutaneously or orally, and reach the parasites via the blood stream. On the other hand, tick preparations are preferably administered topically, i.e. to the skin or the pelt of the host animal, and exhibit their anti-tick activity there by contact. It is a difficult undertaking to find active ingredients that are to act in both treatments and which may be applied either systemically or topically or in both ways.

If e.g. helminthic diseases and tick infestation are to be treated simultaneously, proposals for combination preparations have already been made in literature:

In WO 96/25852 for example, there is an overall proposal to use the combination of a benzoylurea with a further active ingredient from the series milbemycin, avermectin, milbemycinoxim, moxidectin, ivermectin, abamectin and doramectin. However, only the combinations lufenuron & milbemycin and fluazuron & milbemycin are mentioned specifically. There is no indication of using a specific combination of a benzoylurea with a macrocyclic compound, as used in the present invention. Furthermore, in European published specification EP-0,242,502, the combination of avermectinen with a further active ingredient from the class of phorphoric acid esters, carbamates, carboxylic acid esters, certain benzoylureas or other known insecticides or acaricides, is proposed for the simultaneous control of insects, acarids and nematodes, albeit in the field of plant protection. This specification specifically proposes e.g. chlorfluazuron (compound IIb, page 3) as the benzoylurea component. This has a certain structural closeness to the fluazuron used according to the invention If now an attempt is made to transfer these experiences from plant protection to usage in the field of veterinary medicine, which is the subject of the present invention, it is quickly established that the spectrum of activity of the proposed combinations has considerable deficiencies as regards the ectoparasites. Although the avermectin portion does lead to very good efficacy against various nematodes, the addition of the proposed benzoylureas does not gove the desired activity in the field of ectoparasites, especially against the most important members of the acarid order (mites and in particular ticks).

It has now surprisingly been found that a relatively slight structural modification to the chlorfluazuron proposed in EP-0,242,502 not only balances out this deficit in activity, but also leads to extremely well tolerated preparations which act rapidly and persistently against various helminthic diseases and against ticks and mites, and in this way are eminently suitable for usage in the field of animal health. In addition, administration to cattle and sheep shows that these new combination preparations do not have an adverse effect on the normal behaviour of the animals among one another, nor in their eating habits. The new combinations may therefore be used not only curatively, but also preventatively and also over longer periods of time when there is an increased risk of infestation, without the appearance of negative side effects which would harm the animals.

The benzoylureas proposed in EP-0,242,502 are notable structurally for the para-phenoxy- or para-pyridyloxyphenyl group. One notable benzoylurea is e.g. the following substance (A) [in EP-0,242,502=substance IIb, page 3]:

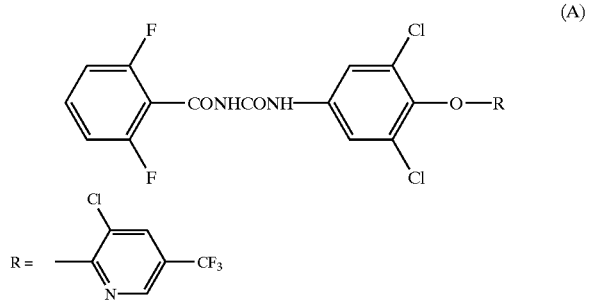

By combining this substance (A) with typical representatives of avermectin derivatives, it is established in the case of the combination with ivermectin, doramectin and moxidectin that they are not suitable for usage in animal health, since although they eliminate the parasitic worms rapidly and persistently, they clearly have no influence on ticks.

By comparing the biological activity of these combinations depicted in the prior art with that of the proposed combinations, which contain as the first component of the mixture likewise ivermectin, doramectin or moxidectin and as the second component the following benzoylurea (B):

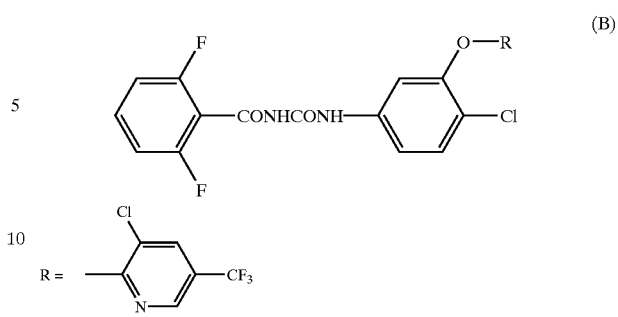

it is established that by using this structural isomer (B), in which also one chlorine atom is missing, a significantly broader spectrum of activity is attained, which is important for veterinary medicine. As well as the frequently appearing worms, it also covers mites and in particular ticks, and when administered at dosages which are effective against the target parasites, it does not create any undesired side effects. In addition, it is surprisingly established that the combinations according to the invention may be administered systemically and topically.

The following examples serve to clarify the invention further, without limiting it in any way.

BIOLOGICAL EXAMPLE

For the sake of simplicity, the chicken mite *Dermanyssus gallinae* is used. This is a good model for determining the effect on ticks.

In vitro Effect on *Dermanyssus gallinae*

The test is carried out with serial dilutions [avermectin component in concentrations of (32), 10, 3.2, 1.0, 0.32 to 0.0001 ppm; the 1-[4-chloro-3-(3-chlor-5-trifluoromethyl-2-pyridyloxy)phenyl]-3-(2,6-difluorobenzoyl)urea in concentrations of 100, 32, 10, 3.2, 1.0, 0.32 and 0.1 ppm]. For the test, the lowest concentration of one active substance is combined with the lowest concentration of the other active substance, and the limits of activity thus worked out. Ten fully engorged female mites of the genus *Dermanyssus gallinae* adhered to a plastic adhesive film are brought into contact with 50 μl of an aqueous suspension or emulsion of the test combination in question. After drying, the film is stuck onto a glass disc. This creates a kind of air bubble around each mite, the lower surface of which is formed by the glass disc and the upper surface by a bulging of the adhesive film. This bubble contains sufficient air for the mite to avoid suffocating. After 5 days, the effect of the test substance is evaluated with the aid of a stereomicroscope by assessing the effect on mortality, oviposition, egg quality, hatching rate, pupation rate, and development of protonymphs according to the following 4 criteria:

1) if 9 to 10 mites are dead, this indicates a lethal effect (characterised by M);
2) if 2 or more mites survive, but do not produce any eggs, this indicates sterility (S);
3) if 2 or more mites survive and produce eggs, but no larvae hatch from these eggs and no protonymphs develop, this indicates a development-inhibiting effect (H);
4) if 2 or more mites survive and lay the usual number of normal eggs, from which larvae hatch and develop into protonymphs, this indicates no activity (−).

In each test, two basic suspensions/emulsions (without active ingredient) and one suspension/emulsion with only one of each component are also tested in the corresponding concentrations.

The test is repeated three times with the following combinations and the results determined. The final result is given in Tables 1 to 3, whereby in the tables marked with a the combinations from the prior art are listed and in the tables marked with b the results of the combinations according to the invention are listed.

TABLE 1

Combination of ivermeciin and A against *Dermanyssus galinae*

| ppm | Ivermectin⇒ | | | | | | | | |
|---|---|---|---|---|---|---|---|---|---|
| | 0.001 | 0.0032 | 0.01 | 0.032 | 0.1 | 0.32 | 1 | 3.2 | 10 |
| A⇓ | | | | | | | | | |
| 100 | — | — | — | — | 90% H | 100% H | 90% S | 100% M | 100% M |
| 32 | — | — | — | 80% H | 80% H | 10% &H | 80% M | 100% M | 100% M |
| 10 | — | — | — | 80% H | 80% H | 100% H | 80% M | 100% M | 100% M |
| 3.2 | — | — | — | — | 100% H | 100% H | 80% M | 100% M | 100% M |
| 1 | — | — | — | — | 80% H | 100% H | 80% M | 100% M | 100% M |
| 0.32 | — | — | — | — | 90% H | 100% H | 80% M | 100% M | 100% M |
| 0.1 | — | — | — | 80% H | 60% H | 100% H | 90% M | 100% M | 100% M |
| B⇓ | | | | | | | | | |
| 100 | 100% H | 100% H | 100% H | 100% H | 100% H | 100% H | 100% H | 100% M | 100% M |
| 32 | 100% H | 90% H | 100% H | 90% H | 100% H | 100% H | 100% H | 100% M | 100% M |
| 10 | 80% H | 90% H | 90% H | 80% H | 100% H | 100% H | 100% H | 100% M | 100% M |
| 3.2 | 70% H | 80% H | 80% H | 80% H | 100% H | 100% H | 100% H | 100% M | 100% M |
| 1 | — | — | — | 70% H | 100% H | 100% H | 80% H | 100% M | 100% M |
| 0.32 | — | — | — | — | 90% H | 90% H | 90% H | 100% M | 100% M |
| 0.1 | — | — | — | — | 80% H | 100% H | 100% H | 100% M | 100% M |

TABLE 2

Combination of moxidectin and A against *Dermanyssus galinae*

| ppm | moxidectin⇒ | | | | | | | | |
|---|---|---|---|---|---|---|---|---|---|
| | 0.0032 | 0.01 | 0.032 | 0.1 | 0.32 | 1 | 3.2 | 10 | 32 |
| A⇓ | | | | | | | | | |
| 100 | — | — | — | — | — | 100% H | 100% H | 100% H | 100% S |
| 32 | — | — | — | — | 80% H | 100% H | 100% H | 100% H | 100% S |
| 10 | — | — | — | — | 90% H | 100% H | 100% H | 100% H | 100% S |
| 3.2 | — | — | — | — | — | 100% H | 90% H | 100% H | 90% S |
| 1 | — | — | — | — | 100% H | 100% H | 100% H | 90% H | 100% M |
| 0.32 | — | — | — | — | 90% H | 100% H | 100% H | 100% H | 100% S |
| 0.1 | — | — | — | — | 100% H | 100% H | 100% H | 100% H | 100% S |
| B⇓ | | | | | | | | | |
| 100 | 100% H | 100% H | 100% H | 100% H | 100% H | 100% H | 100% H | 100% M | 100% S |
| 32 | 100% H | 90% H | 90% H | 100% H | 80% H | 100% H | 100% H | 100% M | 100% S |
| 10 | 100% H | 100% H | 80% H | 100% H | 90% H | 100% H | 90% H | 100% M | 100% S |
| 3.2 | 70% H | 100% H | 100% H | 100% H | 100% H | 100% H | 90% H | 100% M | 100% S |
| 1 | — | — | 60% H | 100% H | 100% H | 100% H | 90% H | 100% M | 90% S |
| 0.32 | — | — | — | 80% H | 90% H | 90% H | 100% H | 90% M | 100% M |
| 0.1 | — | — | — | 70% H | 90% H | 100% H | 100% H | 100% M | 100% S |

TABLE 3

Combination of doramectin and A against *Dermanyssus galinae*

| ppm | doramectin⇒ | | | | | | | | |
|---|---|---|---|---|---|---|---|---|---|
| | 0.001 | 0.0032 | 0.01 | 0.032 | 0.1 | 0.32 | 1 | 3.2 | 10 |
| A⇓ | | | | | | | | | |
| 100 | — | — | — | — | 60% H | 80% H | 100% H | 100% S | 100% M |
| 32 | — | — | — | — | 60% H | 100% H | 100% H | 100% S | 100% M |
| 10 | — | — | — | — | 90% H | 90% H | 100% H | 100% M | 100% M |
| 3.2 | — | — | — | — | 80% H | 100% H | 100% H | 100% S | 100% M |
| 1 | — | — | — | — | 90% H | 100% H | 90% H | 100% S | 90% M |

TABLE 3-continued

Combination of doramectin and A against *Dermanyssus galinae*

| ppm | doramectin⇒ 0.001 | 0.0032 | 0.01 | 0.032 | 0.1 | 0.32 | 1 | 3.2 | 10 |
|---|---|---|---|---|---|---|---|---|---|
| 0.32 | — | — | — | — | 100% H | 90% H | 100% H | 90% S | 100% M |
| 0.1 | — | — | — | — | 90% H | 100% H | 90% H | 100% S | 100% M |
| B⇓ | | | | | | | | | |
| 100 | 100% H | 100% H | 100% H | 100% H | 100% H | 100% H | 100% H | 100% S | 100% M |
| 32 | 80% H | 90% H | 90% H | 80% H | 80% H | 100% H | 100% H | 100% S | 100% M |
| 10 | 100% H | 100% H | 80% H | 80% H | 90% H | 100% H | 90% H | 100% M | 100% M |
| 3.2 | 70% H | 60% H | 100% H | 100% H | 100% H | 100% H | 90% H | 100% S | 100% M |
| 1 | — | — | — | 90% H | 100% H | 100% H | 90% H | 90% S | 100% M |
| 0.32 | — | — | — | 70% H | 90% H | 90% H | 100% H | 100% S | 100% M |
| 0.1 | — | — | — | 80% H | 90% H | 100% H | 100% H | 100% H | 100% M |

All the basic suspensions/emulsions (without active ingredient) show no biological activity, and also no secondary reactions. The active ingredient (A) of the prior art shows no activity at any concentration; the avermectin components ivermectin, moxidectin and doramectin achieve full activity at 0.32 and 10 ppm in terms of preventing oviposition. 1-[4-chloro-3-(3-chloro-5-trifluoromethyl-2-pyridyloxy)phenyl]-3-(2,6-difluorobenzoyl)urea prevents oviposition up to a concentration of 0.01 ppm.

The comparison clearly shows that the combinations according to the invention (compare tables 1 b, 2b and 3b with 1a, 2a and 3a) are active against *Dermanyssus gallinae* at substantially lower threshold concentrations than the corresponding comparison combination from the prior art. Individual tests with the tick *Boophilus microplus* show a completely analogous manifestation and the first in vivo tests on sheep confirm the targeted activity. In vitro tests against nematodes (*Haemonchus contortus*) show that the mixing of substance (B) with the avermectin component has no effect on its antihelminthic activity.

It has also been found that certain forms of application, for example external application, but especially systemic administration of the combination according to the invention and where appropriate with the addition of one or more compounds from other substance classes, e.g. methoprene, hydroprene, dicyclanil and cythioate, or their salts, to potentiate the effect, can eliminate the said ectoparasites very rapidly and completely, thus intervening to block the complex development cycle, and at the same time achieving an efficient control of the endoparasites, especially nematodes. The combinations and preparations according to the invention exert their excellent parasiticidal effect in full when given to the host animal systemically, i.e. orally, parenterally, subcutaneously, intramuscularly or intravenously. It is thus now possible, through selective periodic administration of these compounds, to prevent the constant reinfestation of the host animals with the various parasites in a simple manner and to keep the parasites at bay from the herds for a long time. The parasites are either killed by contact or are prevented from reproducing, or the juvenile stages are prevented from growing and die prematurely.

A further preferred object of the invention is thus also a method of simultaneously controlling nematodes, mites and ticks in and on domestic animals, productive livestock and pets, in which the active ingredient combination according to the invention or a preparation of veterinary medicine which contains the combination is administered to the host animal orally, parenterally or by implant in an amount that is effective against the parasites.

Essential to the invention is the fact that the combination or the preparation of the invention is administered in such a way that the active ingredients which the composition comprises can be taken up in sufficient quantity with the blood of the host animal by endoparasites, ectoparasites and other parasites which can be regarded as vectors for the transmission of endoparasites, so that the eggs laid by the adult parasites and/or the larvae hatching therefrom are not able to develop.

This is achieved with the combination or preparation of the invention using different forms of application, e.g. through the oral administration of the preparations containing the active ingredients. In this case, formulated means e.g. in the form of a powder, a tablet, a granulate, a capsule, an emulsion, a foam, in micro-encapsulated form, etc., whereby as already mentioned, the preparation does not necessarily have to be given to the animal directly, but may also be mixed with its food. Of course, all compositions to be administered orally may contain further additives, in addition to conventional formulation excipients. These additives encourage willing consumption by the host animal, for example suitable odorous substances and flavourings. Because of its simple practicability, oral usage is one of the preferred subjects of the invention. A further type of application is parenteral usage, e.g. by subcutaneous or intravenous injection, topical application or as a long-term preparation (depot form) in the form of an implant or injection of microcapsules (so-called "microspheres").

Oral application also includes e.g. administration of animal food, for example dog or cat food, which contains the active substances already mixed therein, e.g. as biscuits, as chews, as water-soluble capsules or tablets, in water-soluble form that can be dripped onto the food, or in other forms that can be mixed with the animal food. The implants also include all the devices which can be inserted into the body of the animal in order to deliver the substance.

Percutaneous application forms include for example the subcutaneous, dermal, intramuscular and even intravenous administration of injectable forms. Apart from the usual injection syringes with needles, needleless systems and pour-on and spot-on formulations may also be expedient.

By choosing a suitable formulation, it is possible to enhance the penetration power of the active ingredients through the living tissue of the animal, and to maintain its availability. This is of importance e.g. if one or more poorly soluble active ingredients are used, the low solubility of which require a solubility-enhancing measure, since the body fluids of the animal are only able to dissolve small amounts of the substance at a time.

Furthermore, the active ingredient combinations may also be present in a matrix formulation, which physically prevents their decomposition and maintains the availability of the active ingredients. This matrix formulation is injected into the body and remains there as a type of depot, from which the active ingredient combination is continuously released. Such matrix formulations are known to the person skilled in the art. These are generally waxy, semi-solid excipients, for example plant waxes and polyethylene glycols with a high molecular weight or copolymers of degradable polyesters.

Good availability of the active ingredient combination is also achieved by inserting an implant of the active substances into the animal. Such implants are widely used in veterinary medicine and often consist of silicone-containing rubber. Here, the active substances are dispersed in the solid rubber or are found in the inside of a hollow rubber element. Care must be taken that active substances are selected, which are soluble in the rubber implant, since they are first dissolved in the rubber and then continuously seep from the rubber material to the body fluids of the animal to be treated.

The rate of release of the active substances from the implant, and thus the time span during which the implant shows activity, is generally determined by the accuracy of measurement (amount of active ingredient in the implant) of the implant, the environment of the implant and the polymer formulation from which the implant is made.

The administration of the active ingredients by means of an implant represents a further preferred constituent of the present invention. This type of administration is extremely economical and effective, because a correctly dimensioned implant guarantees a constant concentration of the active substance in the tissue of the host animal. Nowadays, implants can be designed and implanted in a simple manner, so that they are in a position to deliver the active ingredients over some months.

The administration of veterinary medicine additives to animal food is best known in the field of animal health. Usually, first of all, a so-called premix is produced, in which the active substances are dispersed in a liquid or finely distributed in solid carriers. This premix can normally contain about 1 to 800 g of the active ingredient combination per kg, depending on the desired end concentration in the food.

It is known moreover that active ingredients can be hydrolysed or their effects attenuated by the constituents of the feed under unfavourable circumstances. This may be prevented by incorporating them in a protective matrix, for example gelatin.

The combinations according to the invention are suitably applied in a dosage of 0.01 to 800, preferably 0.1 to 200, especially 0.5 to 50 mg/kg body weight based on the host animal, the amounts referring to the sum of both active substances.

A good dose of the combination of the invention which can be administered regularly to the host animal is especially 2.5–5 mg/kg body weight in the cat and 0.5–15 mg/kg per kg body weight in the dog. In the sheep, it is 0.5–30 mg/kg body weight and in the cow it is 1–30 mg/kg body weight. It is expedient to carry out the administration at regular intervals, e.g. every few days, weekly, or monthly.

The total dose can vary both between and within animal species, since the dose depends among other things on the weight and the constitution of the animal.

For the formulation of compositions that are to be administered to humans, domestic animals, livestock, and pets, the adjuvants known from veterinary practice for oral, parenteral and implant forms can be used. The following is a non-exhaustive list of some examples.

The active ingredient combinations according to the invention contain 1-[4-chloro-3-(3-chloro-5-trifluoromethyl-2-pyridyloxy)phenyl]-3-(2,6-difluorobenzoyl)urea [compound B] and a compound of formula (i) [Verbindung (i)] in almost any proportion, but preferably in a mixture ratio of B:1 of 100,000:1 to 1:100, especially in a ratio of 10:1 to 1:100, advantageous active ingredient concentrations being ca. 100–1 ppm of B to 0.1–10 ppm of (i).

Compositions or preparations to be used according to the invention normally contain 0.1 to 99% by weight, especially 0.1 to 95% by weight of a combination of the compound 1-[4-chloro-3-(3-chloro-5-trifluoromethyl-2-pyridyloxy) phenyl]-3-(2,6-difluorobenzoyl)urea and a compound of formula (i) and 99.9 to 1% by weight, especially 99.9 to 5% by weight of a solid or liquid, physiologically acceptable carrier, including 0 to 25 Gew.-%, especially 0.1 to 25% by weight of a non-toxic surfactant.

Suitable carriers are in particular fillers, such as sugars, e.g. lactose, saccharose, mannitol or sorbitol, cellulose preparations and/or calcium phosphates, e.g. tricalcium phosphate or calcium hydrogen phosphate, in a broader sense also binders, such as starch pastes using e.g. corn, wheat, rice or potato starch, gelatin, tragacanth, methyl cellulose and/or, if desired, disintegrants, such as the above-mentioned starches, in a broader sense also carboxymethyl starch, cross-linked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Tablet cores may be provided with suitable, where appropriate enteric, coatings, using inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavours or pigments may be added to the tablets or tablet coatings, for example for identification purposes or to indicate different doses.

Further orally administrable pharmaceutical compositions include hard capsules consisting of gelatin, and also soft, sealed capsules consisting of gelatin and a plasticizer, such as glycerol or sorbitol. The hard capsules may contain the active ingredients in the form of granules, for example in admixture with fillers, such as lactose, binders, such as starches, and/or glidants, such as talc or magnesium stearate, and where appropriate stabilisers. In soft capsules, the active ingredients are preferably dissolved or suspended in suitable liquids, such as fatty oils, paraffin oil, or liquid polyethylene glycols, and stabilisers may likewise be added. Amongst other forms, capsules which can be both easily chewed and also swallowed whole are preferred.

The formulations suitable for parenteral administration are especially aqueous solutions of the active ingredient combinations in water-soluble form, e.g. water-soluble salts, in the broader sense also suspensions of the active ingredients, such as appropriate oily injectable suspensions using suitable lipophilic solvents or vehicles, such as oils, e.g. sesame oil, or synthetic fatty acid esters, e.g. ethyl oleate, or triglycerides, or aqueous injectable suspensions containing viscosity-increasing agents, e.g. sodium carboxymethyl cellulose, sorbitol and/or dextran, and where appropriate stabilisers.

The preparations of the invention may be prepared in a manner known per se, for example by means of conventional mixing, granulating, coating, dissolving or lyophilising processes. Veterinary preparations for oral administration can be obtained, for example, by combining the active ingredient combination with solid carriers, granulating a resulting mixture where appropriate, and processing the mixture or granules, if desired or necessary, to form tablets or tablet cores following the addition of suitable excipients.

In the following formulation examples for usage on domestic animals, productive livestock and pets, the term "active ingredient combinations" represents a 1:1 combination of 1-[4-chloro-3-(3-chloro-5-trifluoromethyl-2-pyridyloxy)phenyl]-3-(2,6-difluorobenzoyl)urea and ivermectin.

Tablets: containing one of the active ingredients of formula I may be produced as follows:

| Constituents (for 1000 tablets) | |
|---|---|
| active ingredient combination | 25 g |
| lactose | 100.7 g |
| wheat starch | 6.25 g |
| polyethylene glycol 6000 | 5.0 g |
| talc | 5.0 g |
| magnesium stearate | 1.8 g |
| demineralised water | q.s. |

Preparation: First of all, all solid ingredients are forced through a sieve of 0.6 mm mesh size. Then, the active ingredient combination, the lactose, the talc and half of the starch are admixed. The other half of the starch is suspended in 40 ml of water and this suspension is added to a boiling solution of the polyethylene glycol in 100 ml of water. The starch paste obtained is added to the principle amount and the mixture granulated, if necessary adding water. The granulate is dried over night at 35°, forced through a sieve of 1.2 mm mesh size, mixed with the magnesium stearate and pressed into biconcave tablets of ca. 6 mm diameter.

Tablets: each containing a total of 0.0183 g active ingredient combination are prepared as follows:

| Composition (for 10,000 tablets) | |
|---|---|
| active ingredient combination | 183.00 g |
| lactose | 290.80 g |
| potato starch | 274.70 g |
| stearic acid | 10.00 g |
| talc | 217.00 g |
| magnesium stearate | 2.50 g |
| colloidal silicon dioxide | 32.00 g |
| ethanol | q.s. |

A mixture of an active ingredient combination, the lactose and 274.70 g of potato starch is moistened with an ethanolic solution of the stearic acid and granulated through a sieve. After drying, the remaining potato starch, the talc, the magnesium stearate and the colloidal silicon dioxide are mixed in, and the mixture is pressed into tablets each of 0.1 g weight, which may be provided with dividing notches for finer adjustment of the dosage.

Capsules: each containing a total of 0.022 g active ingredient combination may be prepared as follows:

| Composition (for 1000 tablets) | |
|---|---|
| active ingredient combination | 22.00 g |
| lactose | 249.80 g |
| gelatin | 2.00 g |
| corn starch | 10.00 g |
| talc | 15.00 g |
| water | q.s. |

The active ingredient combination is mixed with the lactose, the mixture wetted evenly with an aqueous solution of the gelatin and granulated through a sieve with a mesh size of 1.2–1.5 mm. The granulate is mixed with the dried corn starch and the talc, and portions of 300 mg are filled into hard gelatin capsules (size 1).

Premix (Feed Additive)

0.16 parts by weight of active ingredient combination 4.84 parts by weight of secondary calcium phosphate, alumina, aerosil, carbonate or calcium carbonate are mixed until homogeneous with 95 parts by weight of an animal feed or 0.41 parts by weight of active ingredient combination 5.00 parts by weight of aerosiylime (1:1) are mixed to homogeneity with 94.59 parts by weight of a commercial dry food.

| Boli: | | |
|---|---|---|
| I | active ingredient combination | 33.00% |
| | methylcellulose | 0.80% |
| | silicic acid, highly dispersed | 0.80% |
| | corn starch | 8.40% |
| II | lactose, cryst. | 22.50% |
| | corn starch | 17.00% |
| | microcryst. cellulose | 16.50% |
| | magnesium stearate | 1.00% |

The methylcellulose is first stirred into water. After the material has swollen, silicic acid is stirred in and the mixture homogeneously suspended. The active ingredient combination and the corn starch are mixed. The aqueous suspension is worked into this mixture and kneaded to a dough. The resulting mass is granulated through a 12 M sieve and dried. In a further step, all 4 adjuvants are thoroughly mixed. Finally, the premixtures resulting from the first two partial steps are mixed and compressed to form boli.

| Injectables A. Oily vehicle (slow release) | | | |
|---|---|---|---|
| 1. | active ingredient combination | 0.1–1.0 g | |
| | groundnut oil | ad 100 ml | |
| 2. | active ingredient combination | 0.1–1.0 g | |
| | sesame oil | ad 100 ml | |

Preparation: The active ingredient combination is dissolved in part of the oil whilst stirring and, if required, with gentle heating, then after cooling made up to the desired volume and sterile-filtered through a suitable membrane filter with a pore size of 0.22 mm.

| B Water-miscible solvent (average rate of release) | |
| --- | --- |
| active ingredient combination | 0.1–1.0 g |
| 4-hydroxymethyl-1,3-dioxolane (glycerol formal) | 40 g |
| 1,2-propanediol | ad 100 ml |
| an active ingredient from table 1 | 0.1–1.0 g |
| glycerol dimethyl ketal | 40 g |
| 1,2-propanediol | ad 100 ml |

Preparation: The active ingredient combination is dissolved in part of the solvent whilst stirring, filled to the desired volume and sterile-filtered through an appropriate membrane all filter with a pore size of 0.22 mm.

| C. Aqueous solubilisate (rapid release) | |
| --- | --- |
| 1. active ingredient combination | 0.1–1.0 g |
| polyethoxylated castor oil (40 ethylene oxide units) | 10 g |
| 1,2-propanediol | 20 g |
| benzyl alcohol | 1 g |
| aqua ad inject. | ad 100 ml |
| 2. active ingredient combination | 0.1–1.0 g |
| polyethoxylated sorbitan monooleate (20 ethylene oxide units) | 8 g |
| 4-hydroxymethyl-1,3-dioxolane (glycerol formal) | 20 g |
| benzyl alcohol | 1 g |
| aqua ad inject. | ad 100 ml |

Preparation: The active ingredient combination is dissolved in the solvents and the surfactant, and made up with water to the desired volume. Sterile filtration through an appropriate membrane filter of 0.22 mm pore size.

| Pour on | | |
| --- | --- | --- |
| A. | active ingredient combination | 5 g |
| | isopropyl myristate | 10 g |
| | isopropanol | ad 100 ml |
| B | active ingredient combination | 2 g |
| | hexyl laurate | 5 g |
| | medium-chained triglyceride | 15 g |
| | ethanol | ad 100 ml |
| C. | active ingredient combination | 2 g |
| | oleyl oleate | 5 g |
| | N-methyl-pyrrolidone | 40 g |
| | isopropanol | ad 100 ml |

The aqueous systems may also preferably be used for oral and/or intraruminal application.

The compositions may also contain further additives, such as stabilisers, e.g. where appropriate epoxidised vegetable oils (epoxidised coconut oil, rapeseed oil, or soybean oil); antifoams, typically silicone oil; preservatives; viscosity regulators; binders; and tackifiers, as well as fertilisers or other chemical agents to achieve special effects.

Further biologically active substances or additives, which are neutral towards the compounds of formula I and do not have a harmful effect on the host animal to be treated, as well as mineral salts or vitamins, may also be added to the described compositions.

What we claim is:

1. A method for controlling parasites on an animal comprising the administration to the animal of an amount of a combination of 1-[4-chloro-3-(3-chloro-5-trifluoromethyl-2-pyridyloxy)phenyl]-3-(2,6-difluorobenzoyl)urea and a compound of formula (i)

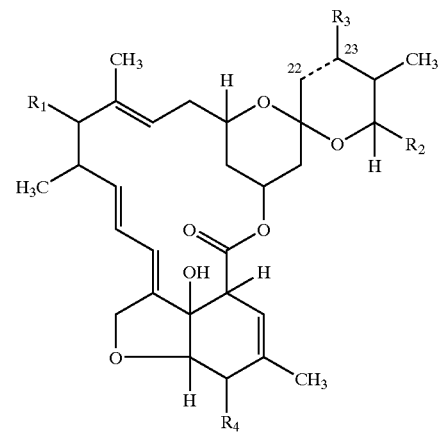

wherein $R_1$ is hydrogen or one of radicals

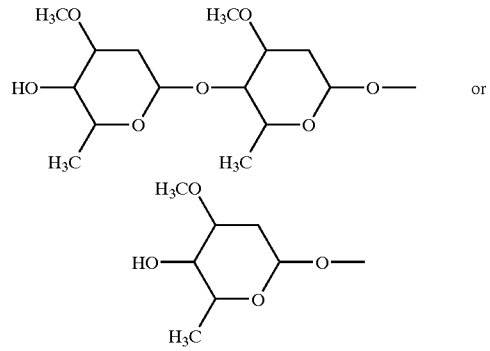

$R_2$ is —CH($CH_3$)—$CH_3$, —CH($CH_3$)—$C_2H_5$, —C($CH_3$)=CH—CH($CH_3$)$_2$ or cyclohexyl; $R_3$ is hydrogen or hydroxy if the bond between atoms 22 and 23 represents a double bond, or is hydrogen or the group =N—O—$CH_3$ if a single bond is present between atoms 22 and 23; and $R_4$ is HO— or HO—N=, in an amount effective for controlling parasites on the animal, and wherein the compound of formula (i) is selected from the group consisting of ivermectin, doramectin, moxidectin and selamectin.

2. The method according to claim 1, wherein the parasite is selected from the group consisting of mites, ticks and nematodes.

3. The method according to claim 1, wherein the the combination is administered systemically.

4. The method according to claim 1 in the control of ecto- and endoparasites on productive livestock, domestic animals and pets, in which the combination is administered sequentially or simultaneously.

5. The method according to claim 4 wherein the combination is administered systemically.

6. The method according to claim 5 in the control of ecto- and endoparasites on productive livestock, domestic animals and pets further comprising the administration of an acceptable carrier.

7. The method according to claim 5 in the systemic control of ecto- and endoparasites on productive livestock, domestic animals and pets.

8. The method according to claim 1, wherein the active ingredient combination contains 1-[4-chloro-3-(3-chloro-5-trifluoromethyl-2-pyridyloxy)phenyl]-3-(2,6-difluorobenzoyl)urea and a compound of formula (I) in a ratio of the mixture of 1:500 to 500:1.

9. The method according to claim 1 wherein the compound of formula (I) is in free form or salt form.

10. The method according to claim 9 wherein the formula (I) is in a physiologically acceptable salt form.

11. A composition for the control of ecto- and endoparasites on productive livestock, domestic animals and pets, comprising 1-[4-chloro-3-(3-chloro-5-trifluoromethyl-2-pyridyloxy)phenyl]-3-(2,6-difluorobenzoyl)urea and a compound of formula (i)

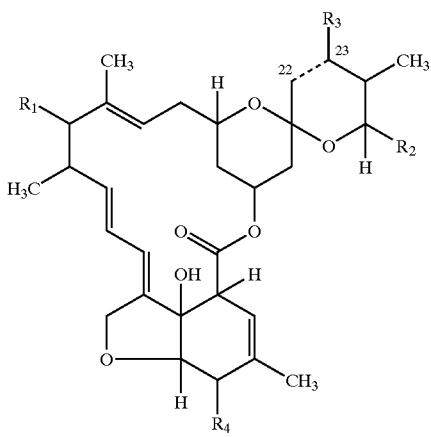

wherein $R_1$ is hydrogen or one of radicals

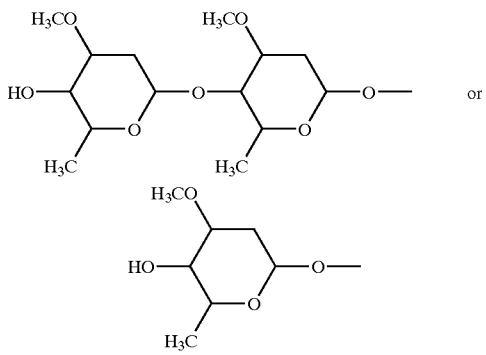

$R_2$ is —CH($CH_3$)—$CH_3$, —CH($CH_3$)—$C_2H_5$, —C($CH_3$)=CH—CH($CH_3$)$_2$ or cyclohexyl; $R_3$ is hydrogen or hydroxy if the bond between atoms 22 and 23 represents a double bond, or is hydrogen or the group =N—O—$CH_3$ if a single bond is present between atoms 22 and 23; and $R_4$ is HO— or HO—N=, in an amount effective for controlling parasites on the animal, and wherein the compound of formula (i) is selected from the group consisting of ivermectin, doramectin, moxidectin and selamectin.

12. The composition according to claim 11 wherein the ratio of the compounds is from 10,000:1 to 1:100.

13. The composition according to claim 12 wherein the ratio of the compounds is from 10:1 to 1:100.

* * * * *

UNITED STATES PATENT AND TRADEMARK OFFICE
CERTIFICATE OF CORRECTION

PATENT NO.    : 6,469,067 B1                                          Page 1 of 1
DATED         : October 22, 2002
INVENTOR(S)   : Bouvier et al.

It is certified that error appears in the above-identified patent and that said Letters Patent is hereby corrected as shown below:

<u>Column 16,</u>
Line 52, change "the the" to -- the --.
Line 65, change "claim 5" to -- claim 1 --.

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,469,067 B1
DATED : October 22, 2002
INVENTOR(S) : Bouvier et al.

It is certified that error appears in the above-identified patent and that said Letters Patent is hereby corrected as shown below:

<u>Title page,</u>
Item [73] Assignee, should read as follows:
-- [73] Assignee: Novartis Animal Health US, Inc., Greensboro, NC (US) --.

Signed and Sealed this

Second Day of September, 2003

JAMES E. ROGAN
*Director of the United States Patent and Trademark Office*